United States Patent [19]

Uhing

[11] 4,231,970

[45] Nov. 4, 1980

[54] REACTION PRODUCTS OF UNSATURATED HYDROCARBONS WITH $P_4S_{10}$ AND $PSX_3$

[75] Inventor: Eugene H. Uhing, Pleasantville, N.Y.

[73] Assignee: Stauffer Chemical Company, Westport, Conn.

[21] Appl. No.: 925,129

[22] Filed: Jul. 17, 1978

[51] Int. Cl.$^3$ .................................................. C07F 9/04
[52] U.S. Cl. .................................... 260/931; 260/139; 260/502.4 P; 260/502.4 R; 260/545 P; 260/972; 568/66
[58] Field of Search ..................... 260/139, 543 P, 972, 260/545 P, 931, 609 R, 502.4 R, 502.4 P

[56] References Cited

U.S. PATENT DOCUMENTS

| 3,897,491 | 7/1975 | Toy et al. | 260/543 P |
| 3,988,368 | 10/1976 | Ura et al. | 260/543 P |

*Primary Examiner*—Anton H. Sutto
*Attorney, Agent, or Firm*—Paul J. Juettner

[57] ABSTRACT

Unsaturated hydrocarbons such as ethylene, propylene, butylene, pentene, cyclohexene and 1,3-butadiene among others are reacted with $P_4S_{10}$ and $PSX_3$, wherein X is selected from the group consisting of Cl and Br, under autogenous pressure at temperatures from about 90° C. to about 250° C. The reaction products obtained are useful as intermediates in preparation of agricultural chemicals; lubricant and polymer additives; mercaptoethyl- and mercaptobutylphosphonic acids; and mercaptobutylphosphinic acids.

5 Claims, No Drawings

REACTION PRODUCTS OF UNSATURATED HYDROCARBONS WITH P₄S₁₀ AND PSX₃

BACKGROUND OF THE INVENTION

1. Field of the Invention

The present invention relates to new compounds which can be characterized as reaction products of unsaturated hydrocarbons with $P_4S_{10}$ and $PSX_3$, wherein X is selected from the group consisting of Cl and Br.

2. The Prior Art

Reactions of ethylene with $P_4S_{10}$ and $PCl_3$ are described in U.S. Pat. No. 3,897,491. The reactions are conducted in an autoclave at elevated temperature to produce alkyl phosphorus halides.

In U.S. Pat. No. 3,988,368 a process for preparing phenylphosphonothioic dichloride is described. The process consists of reacting benzene with $PSCl_3$ in the presence of a catalyst. Suitable catalysts include for example $P_2S_5$ and $PCl_3$ or $AlCl_3$ and $P_2S_5$. The reaction scheme is as follows:

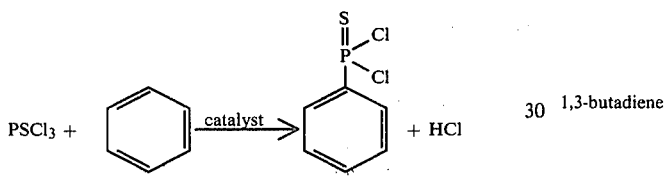

The reactions of unsaturated hydrocarbons with $P_4S_{10}$ and $PSX_3$ as described in the present invention are not disclosed in the prior art.

SUMMARY OF THE INVENTION

In accordance with the present invention, reaction products of unsaturated hydrocarbons with $P_4S_{10}$ and $PSCl_3$ are prepared according to the generalized reaction scheme:

$$R_1R_2C=CR_3R_4 + P_4S_{10} + PSX_3 \rightarrow \text{Products} \qquad I$$

wherein X is selected from the group consisting of Cl and Br and $R_1, R_2, R_3$ and $R_4$ can be the same or different and are selected from the group consisting of hydrogen, $C_1-C_{10}$ alkyl and $C_1-C_{10}$ alkylene with the proviso that the unsaturated hydrocarbon reactant $$R_1R_2C=CR_3R_4 \qquad (1)$$

can be a cyclic compound.

The reaction is conducted under autogenous pressure at temperatures from about 90° C. to about 250° C.

Products of the reaction are useful as intermediates in preparation of agricultural chemicals; lubricant and polymer additives; mercaptoethyl- and mercaptobutylphosphonic acids; and mercaptobutylphosphinic acids.

DETAILED DESCRIPTION OF THE INVENTION

Exemplary unsaturated hydrocarbons and the corresponding reaction products of the present invention include, but are not limited to the following:

| UNSATURATED HYDROCARBON | REACTION PRODUCT |
| --- | --- |
| $CH_2=CH_2$ | $+SCH_2CH_2P(S)S+_x$ and $+SP(S)CH_2CH_2P(S)S+_x$ where $x \geq 1$ |
| $CH_2=CH-CH_3$ | 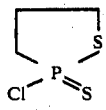 |
| 1 OR 2 BUTENE | 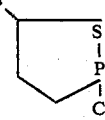 |
| 1-pentene | 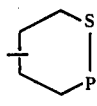 |
| cyclohexene | 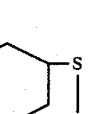 or isomers |
| 1,3-butadiene | 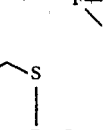 |
| isoprene | 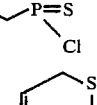 and 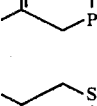 |

The method of the present invention comprises contacting an unsaturated hydrocarbon reactant of the general formula:

$$R_1R_2C=CR_3R_4 \qquad (1)$$

wherein $R_1, R_2, R_3$ and $R_4$ can be the same or different and are selected from the group consisting of hydrogen, $C_1-C_{10}$ alkyl and $C_1-C_{10}$ alkylene with the proviso that said reactant can be a cyclic compound; with other reactants having the general formulas:

$$P_4S_{10} \qquad (2); \text{ and}$$

$$PSX_3 \text{ and optionally } PX_3 \qquad (3)$$

wherein X is selected from the group consisting of Cl and Br.

Reactants utilized in the method of the present invention are generally employed in stoichiometric amounts, although an excess of any reactant can be used if desired. The quantity of undesired side products however, is minimized by the use of approximately stoichiometric amounts of reactants. No catalyst is used or necessary in the method of the present invention.

The method is carried out at elevated temperature and pressure. The reaction temperature is from about 90° C. to about 250° C. Reaction pressure is autogenous and is generally from about 2 to about 300 atmospheres.

Reaction times can vary over relatively wide ranges and can easily be determined by one skilled in the art. Factors affecting reaction time include reactant concentration, temperature and pressure. Increases in temperature and reactant concentration result in decreased reaction times. Dilute reactants require longer reaction times than concentrated reactants. Pressure increases reduce reaction time. Typical reaction times are from about 1 to about 24 hours.

The method described above can conveniently be effected by introducing the individual reactants into any reaction zone that can withstand the reaction pressure and be heated to the reaction temperature. A high pressure autoclave rated up to 5000 psig may be required to withstand the pressure generated at reaction temperatures.

Without intending to be bound thereby, the theory of the present invention is as follows:

There are two basic types of unsaturated hydrocarbons that can be used as starting materials in accordance with the present invention. One type is mono-unsaturated containing one

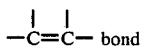
$$-\overset{|}{C}=\overset{|}{C}- \text{ bond}$$

and the other is 1,3-dienes containing two conjugated

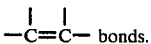
$$-\overset{|}{C}=\overset{|}{C}- \text{ bonds.}$$

The first member of the mono-unsaturated series, $CH_2=CH_2$ is a special case in that all of the hydrogens present are on carbons having double bonds. This causes variations in the reaction based upon reaction conditions. At high temperatures (from about 200° to about 250° C.) the following reaction procedes in high yields:

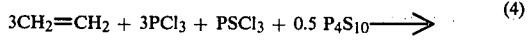
$$3CH_2=CH_2 + 3PCl_3 + PSCl_3 + 0.5\ P_4S_{10} \longrightarrow \quad (4)$$

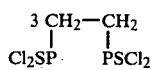
$$3\ \underset{Cl_2SP}{\overset{|}{CH_2}}-\underset{PSCl_2}{\overset{|}{CH_2}}$$

at lower reaction temperatures (from about 130° to about 170° C.) a glossy solid is formed as shown in the following example:

$$4CH_2=CH_2 + P_4S_{10} \rightarrow [C_8H_{16}P_4S_{10}] \quad (5)$$

This product cannot be distilled or sublimed due to the likely formation of a complex high molecular weight compound which still contains the basic $P_4S_{10}$ structure. The reaction is fairly specific in the amount of ethylene that reacts for each $P_4S_{10}$ present. When excess ethylene is added to the reaction mixture it remains unreacted.

Hydrolysis of the low temperature product with hot water gives the following products per starting $P_4S_{10}$:

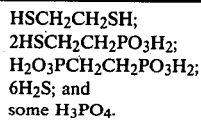

$HSCH_2CH_2SH$;
$2HSCH_2CH_2PO_3H_2$;
$H_2O_3PCH_2CH_2PO_3H_2$;
$6H_2S$; and
some $H_3PO_4$.

When the low temperature reaction is conducted in the presence of $PSCl_3$, the same basic phosphorus acids are found on hydrolysis along with more $H_3PO_4$. Since $H_2O_3PCH_2CH_2PO_3H_2$ is found, there is an indication that some ethylenes reacted to form a $PCH_2CH_2P$ intermediate.

Mono-unsaturated hydrocarbons above ethylene react differently. For example, propylene which has three allylic hydrogens yields the following possible intermediate

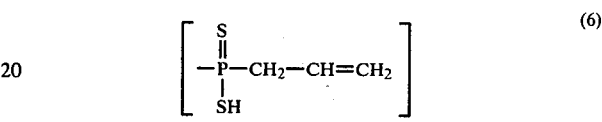
$$\left[ \begin{array}{c} S \\ \| \\ -P-CH_2-CH=CH_2 \\ | \\ SH \end{array} \right] \quad (6)$$

This reaction appears to take place at temperatures of about 100° C. The next step of the reaction is the addition of the SH to a double bond. For all compounds except the propylene this then results in the formation of a cyclic compound. In the case of propylene, however, the following intermediate is formed:

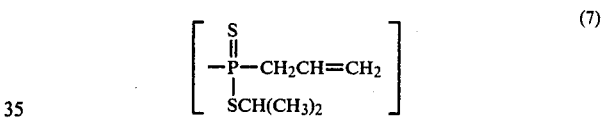
$$\left[ \begin{array}{c} S \\ \| \\ -P-CH_2CH=CH_2 \\ | \\ SCH(CH_3)_2 \end{array} \right] \quad (7)$$

When $PSCl_3$ is present in the reaction with propylene the above intermediates (6) and (7) give the following products in low yield:

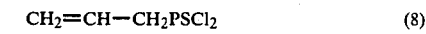
$$CH_2=CH-CH_2PSCl_2 \quad (8)$$
$$(CH_3)_2CHSPSCl \quad (9)$$
$$\overset{|}{CH_2}-CH=CH_2$$

There are various possible reasons why a cyclic compound is not formed readily from the compound of equation (6). For example, a 4-membered ring having the equation

$$\begin{array}{c} H \\ | \\ CH-C-CH_3 \\ | \quad | \\ P-S \end{array} \quad (10)$$

would be strained and therefore not readily formed.

With 1-butene, a cyclic product is formed from an intermediate as follows:

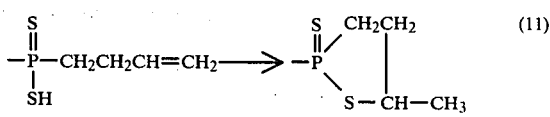
$$\underset{SH}{\overset{S}{\underset{\|}{-P}}}-CH_2CH_2CH=CH_2 \longrightarrow -\underset{S-CH-CH_3}{\overset{S}{\underset{\|}{P}}}\diagdown\overset{CH_2CH_2}{\diagup} \quad (11)$$

The 1,3-dienes appear to react according to the present invention under a new Diels-Alder mechanism in which P═S of the P$_4$S$_{10}$ acts as the dienophile to which a 1,3-diene undergoes a 1,4 cycloaddition. This produces a product having the formula:

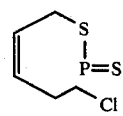 (12)

Several conjugated dienes can be used as starting materials pursuant to the present invention. A general equation for these materials is as follows:

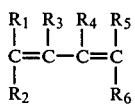 (13)

where R$_1$, R$_2$, R$_3$, R$_4$, R$_5$ and R$_6$ can be the same or different and are selected from the group consisting of H; saturated and aromatic hydrocarbons; >C═C—C═C<; Cl; F; —C≡N; oxygen and sulfur containing ethers and esters; tertiary amines; and groups such as PR; Si(OR)$_x$; S(O)(OR)$_x$(R)$_y$ and B(R)$_x$ where R is a hydrocarbon and x and y are intergers.

Hydrolysis of the various reaction products of the present invention can give numerous acids. The following are examples:

$$CH_2-CH=CH-PO_3H_2$$
$$\phantom{CH_2-CH=CH-}|$$
$$\phantom{CH_2-CH=CH-}PO_3H_2$$

$$CH_3-CH-CH_2CH_2PO_3H_2$$
$$\phantom{CH_3-CH}|$$
$$\phantom{CH_3-CH}SH$$

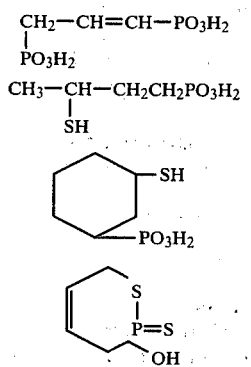

Products of the reaction can be purified by vacuum distillation and other conventional methods such as extraction, sublimation and crystallization.

Identification of products can be achieved by infrared spectra, $^1$H nuclear magnetic resonance spectra, $^{31}$P nuclear magnetic resonance spectra, boiling point analysis and elemental analysis.

Typical yields of the method of the present invention are from about 10% to about 90% based upon phosphorus reacted.

The products of the present invention are useful as intermediates in preparation of agricultural chemicals; lubricant and polymer additives; mercaptoethyl- and butylphosphonic acids; and mercaptobutylphosphinic acids. For example, a cyclic acid chloride produced in accordance with the present invention can be reacted with an alcohol in the presence of an amine to form lubricant and polymer additives as follows:

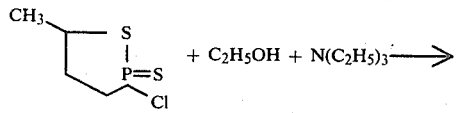 + C$_2$H$_5$OH + N(C$_2$H$_5$)$_3$ ⟶

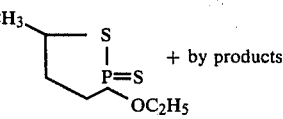 + by products

The present invention will be more fully illustrated in the Examples which follow.

EXAMPLE I

In a 300 ml 316 stainless steel autoclave were placed 28 g 1-butene (0.5 moles), 28 g PSCl$_3$ (0.1666 mole) and 36.9 g P$_4$S$_{10}$ (0.0833 mole). The autoclave was heated at 200° C. for 18 hours. The crude yield of product was 86 g. The product was isolated by distillation having a boiling point of 82° C. at 0.01 mm Hg pressure. The yield of product was 58.4 g or 63% theory.

Analysis: calculated for C$_4$H$_8$ClPS$_2$: 19.0 Cl; 16.6 P; 34.3 S. Found: 19.5 Cl; 16.4 P; 34.8 S.

n$_D^{25}$: 1.6133.

$^{31}$P-nmr δ doublet 117.4, 118.1 ppm (two isomers present due to different CH$_3$ positions).

Hydrolysis of

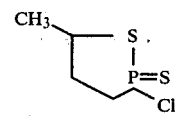

was then conducted to give $$CH_3CH_2CH_2CH_2P(O)(OH)_2$$
$$\phantom{CH_3CH_2CH_2CH_2P(O)(O}|$$
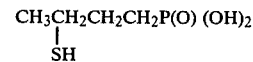

as follows.

A 92.9 g sample of product was hydrolyzed in 500 ml of refluxing 20% HCl for 2 days. The solvent was evaporated to yield 80.3 g white solid product having a 95% yield. A sample was crystallized from etherheptane. Melting point was 142.°-143° C.

Analysis: calculated for C$_4$H$_{11}$O$_3$PS: 28.24 C; 6.47 H; 18.2 P; 18.8 S. Found: 28.0 C; 6.4 H; 18.1 P; 19.15 S.

The product was titrated with aqueous NaOH which showed a dibasic acid of MW 170. Theory for

| | CH$_3$CHCH$_2$CH$_2$PO$_3$H$_2$ = 170. | |
| | \| | |
| | SH | |
| | $^{31}$P-nmr δ = 30.7 ppm | |
| $^{13}$C-nmr | δ (ppm) | J(Hz) |
|---|---|---|
| | 36.8 | 18 |
| | 34.4 | 4 |
| | 25.5 | 135 |
| | 24.4 | 0 |

One sulfur was then removed as follows:

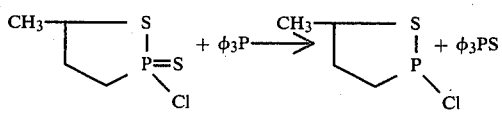

37.3 g C$_4$H$_8$ClPS$_2$ (0.2 moles) and 54.2 g φ$_3$P (0.2 mole) were placed in a 250 ml distillation flask. The mixture was heated to 80° C. This was followed by solidification of the reactants due to formation of φ$_3$PS. The product was distilled under 0.1 mm Hg pressure to give 28.5 g or 92.2% yield.

$n_D{}^{25} = 1.5790$ $^{31}$P-nmr = doublet 168.7 and 163.3 ppm

Hydrolysis of this product in aqueous HCl yielded.

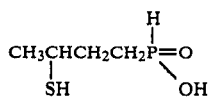

based on H-nmr, $^{31}$P-nmr and $^{13}$C-nmr spectra. $^{31}$P-nmr $\delta = 128.1$ ppm.

Repeating the above process using cis-2-butene instead of 1-butene the distilled yield of product was 55.5 g or 59.5% yield.

It had the same $n_D{}^{25}$ and $^{31}$P-nmr spectra as the above product.

Again repeating the first process bove, using trans-2-butene instead of 1-butene the distilled yield of product was 56.2 g or 60.3% theory.

It had the same $n_D{}^{25}$ and $^{31}$P-nmr spectra as the other products.

EXAMPLE II

In a 300 ml 316 stainless steel autoclave were placed 52.5 g 1-pentene (0.75 mole), 42.25 g $PSCl_3$ (0.25 mole) and 55.5 g $PRS_{10}$ (0.125 mole). The autoclave was heated at 200° C. for 18 hours. The crude yield was 142 g. The crude product was distilled to give 90 g material having a boiling point range of 111°–160° C. at 0.05 mm Hg pressure. Analysis by $^{31}$P-nmr indicate 5 different phosphorus compounds were present. This material was redistilled at 0.1 mm Hg pressure and 9 different fractions taken have a boiling range of 91° to 97° C. Fraction number 8 (9.2 g) assayed 72% cyclic product based on $^{31}$P-nmr ($\delta$ = close doublet at 115.9 ppm) $n_D{}^{25} = 1.6006$.

EXAMPLE III

In a 300 ml 316 stainless steel autoclave were placed 61.5 g cyclohexene (0.75 mole), 42.25 g $PSCl_3$ 0.25 mole) and 44.4 g $P_4S_{10}$ (0.1 mole). The autoclave was heated at 200° C. for 12 hours. The crude yield was 137 g. The product was distilled at 0.05 mm Hg pressure to give 47 g of material having a boiling point of 135°–140° C. Yield = 34%. This material crystallized on cooling. It had a melting point of 73°–76° C. It was crystallized from hot heptane to give material having melting point of 75°–77° C.

Analysis: calculated for $C_6H_{10}ClPS_2$: 16.7 Cl; 14.6 P; 29.2 S. Found: 16.6 Cl; 13.4 P; 29.7 S. $^{31}$P-nmr $\delta = 122.8$ ppm Found: $^{13}$C-nmr

| $\delta$ (ppm) | J(Hz) |
|---|---|
| 19.1 | singlet |
| 28.2 | singlet |
| 33.5 | singlet |
| 39.1 | doublet (11) |
| 52.2 | doublet (50) |
| 56.5 | doublet (3) |

Using the same reaction conditions, several runs were made in which the reactant ratios were changed. The results are listed below:

| Cyclohexene Reaction Study Reactant Molar Ratio | | | |
|---|---|---|---|
| cy-$C_6H_{10}$: | $PSCl_3$: | $P_4S_{10}$: | % Yield |
| 1 | 0.333 | 0.1333 | 34 |
| 1.2 | 0.333 | 0.1333 | 25 |
| 1 | 0.4 | 0.1333 | 24 |
| 1 | 0.333 | 0.16 | 38 |

EXAMPLE IV

In a 300 ml 316 stainless steel autoclave were placed 74 g $P_4S_{10}$ (0.1667 mole); 56.3 g $PSCl_3$ (0.34 mole) and 42 g propylene (1 mole). The autoclave was heated at 240° C. for 8 hours. The crude product was distilled to give

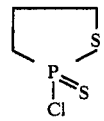

having a boiling point of 66° C. at 0.01 mmHg pressure.

Analysis: calculated for $C_3H_6ClPS_2$: 20.5 Cl; 17.9 P; 37.1 S. Found: 20.6 Cl; 17.4 P; 36.0 S.

$n_D{}^{25} = 1.6367$ $^{31}$P-nmr $\delta = 118$ ppm

EXAMPLE V

In a 300 ml 316 stainless steel autoclave were placed 33.3 g $P_4S_{10}$ (0.075 mole); 101.7 g $PSCl_3$ (0.6 mole); 27.5 g $PCl_3$ (0.2 mole) and 25.2 g propylene (0.6 mole). The autoclave was heated at 125° C. for 12 hours followed by cooling. After cooling, a light tan liquid weighing 183 g was poured out. The product was distilled at 20 mmHg to give 50.3 g unreacted $PCl_3$ and $PSCl_3$ and was then distilled at 0.01 mmHg to give 41.5 g $(CH_3)_2CHSPSCl_2$ and 58.2 g crude $$CH=CH-CH_2PSCl_2$$
$$|$$
$$PSCl_2$$

having a boiling point at 0.1 mmHg of 130°–140° C.

On cooling, the latter fraction formed a crystalline solid which was removed by filtration. The yield of crystalline solid was 20 grams. Melting point was 58°–60° C.

Analysis: calculated for $C_3H_4Cl_4P_2S_2$: 46.1 Cl; 20.1 P; 20.8 S. Found: 45.7 Cl; 20.0 P; 21.0 S.

EXAMPLE VI

In a 300 ml 316 stainless steel autoclave were placed 22.2 g $P_4S_{10}$ (0.05 mole); 67.8 g $PSCl_3$ (0.4 mole); 27.5 g $PCl_3$ (0.2 mole) and 25.2 g propylene (0.6 mole). The autoclave was heated at 130° C. for 12 hours. The crude yield was 122 grams. $^{31}$P-nmr of the crude product gave the following results:

| MATERIAL | $\delta$ | AREA % |
|---|---|---|
| $PCl_3$ | 219 | 49 |
| 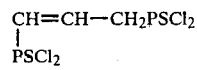 | 97 | 1.7 |
| $CH_2=CH-CH_2PSCl_2$ | 85 | 16 |
| Unknown | 78 | 1 |
| $Cl_2(S)PCH=CH-CH_2PSCl_2$ | 74 | 5 |
|  | 65 |  |
| $(CH_3)_2CHSPSCl_2$ | 70 | 19 |
| $PSCl_3$ | 32 | 8 |

Distillation at 3 mmHg gave 6.7 g of CH₂=CH—CH₂PSCl₂ having a boiling point of 33°-35° C.; n_D²⁰ 1.5516.

EXAMPLE VII

Reactions using 1,3-butadiene were run under various reaction conditions using different reactant ratios. The effect of using a solvent to dilute the reaction and reduce the dimerization of 1,3-butadiene also was determined.

All reactions shown in Table I were run in a 300 ml 316 stainless steel autoclave on a 0.5 mole scale of 1,3-butadiene. All reactions were run for 10 hours. Fifty grams of toluene was added when it was used as a solvent. The reaction conditions and results are shown below. The product was isolated by distillation at 0.1 mm Hg pressure. The product has a boiling point of 109°-110° C. at this pressure. It forms a solid on cooling and can be crystallized from hot heptane. Melting point=63°-66° C.

TABLE I

| TEMP. °C. | REACTANT MOLE RATIO | | | Solvent (toluene) | % Yield |
|---|---|---|---|---|---|
| | C₄H₈: | PSCl₃: | P₄S₁₀ | | |
| 130 | 1 | 0.333 | 0.1667 | no | 36 |
| 150 | 1 | 0.333 | 0.1667 | yes | 50 |
| 150 | 1 | 0.5 | 0.1667 | yes | 54 |
| 150 | 1 | 2 | 0 | no | 0 |
| 180 | 1 | 0.5 | 0.1667 | no | 14 |
| 150 | 1.2 | 0.5 | 0.1667 | yes | 69 |
| 150 | 1.2 | 0.333 | 0.1667 | yes | 69 |
| 150 | 1.2 | 0.333 | 0.1333 | yes | 71 |

³¹P-nmr = 78.5 ppm
H-nmr vinyl to parafin H ratio = 1:2

| ¹³C-nmr = | (P—C) | 44.3 ppm | J = 63 Hz |
|---|---|---|---|
| | (P—S—C) | 33.2 ppm | J = 4.0 Hz |
| | (C=C) | 124.0 ppm | (complex vinyl) |

Analysis: calculated for C₄H₅ClPS₂: 19.2 Cl; 16.8 P; 34.68 S. Found: 19.9 Cl; 16.8 P; 34.4 S.

EXAMPLE VIII

In a 300 ml 316 stainless steel autoclave were placed 29.6 g P₄S₁₀ (0.667 mole); 37.7 g PSCl₃ (0.222 mole); 22.9 g PCl₃ (0.1667 mole); 34 g isoprene (0.5 mole) and 50 g toluene as a diluent. The autoclave was heated at 115° C. for 12 hours. Crude yield was 170 g. The product was isolated by distillation after 106 g of low boilers were removed. Yield was 50 g with a boiling point of 105°-130° C. at 0.01 mmHg.

³¹P-nmr analysis indicated that the product consisted of 79% 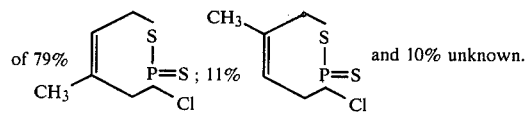 ; 11% and 10% unknown.

Crystallization from heptane gave pure

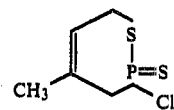

having a melting point of 56°-58° C.
Analysis: calculated for C₅H₈ClPS₂: 17.9 Cl; 15.6 P; 32.2 S. Found: 18.1 Cl; 15.6 P; 32.3 S.
³¹P-nmr δ=83 ppm

| ¹³C-nmr δ (ppm) | J(Hz) |
|---|---|
| 27.5 | doublet (14) |
| 33.1 | doublet (6) |
| 48.8 | doublet (61) |
| 119.2 | doublet (15) |
| 133.3 | doublet (10) |

Having set forth the general nature and some examples of the present invention, the scope is now particularly set forth in the appended claims.

What is claimed is:
1. A composition of the formula:

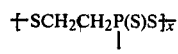

wherein x is ≧1.
2. A composition of the formula:

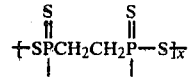

wherein x≧1.
3. A method comprising reacting P₄S₁₀ with ethylene at a reaction temperature of from about 130° C. to about 170° C. under autogenous pressure to form a reaction product characterized as a glossy solid and having an emperical formula [C₈H₁₆P₄S₁₀].
4. The method of claim 3 wherein the reactin product is selected from the group consisting of

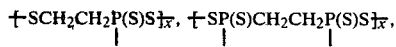

and mixtures thereof where x≧1.
5. The method as recited in claim 3 which further includes the step of hydrolyzing said glossy solid to form a mixture of the following products per starting P₄S₁₀:

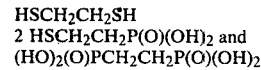

* * * * *